United States Patent [19]

Kada et al.

[11] 4,191,752

[45] Mar. 4, 1980

[54] ISOLATION OF ANTI-MUTAGENIC FACTOR FROM CABBAGE JUICE

[75] Inventors: Tsuneo Kada; Tadashi Inoue, both of Tokyo; Kazuyoshi Morita, Odawara, all of Japan

[73] Assignee: Kanebo, Ltd., Tokyo, Japan

[21] Appl. No.: 940,089

[22] Filed: Sep. 6, 1978

[30] Foreign Application Priority Data

Mar. 9, 1978 [DE] Fed. Rep. of Germany ....... 2810293
Mar. 14, 1978 [JP] Japan ................................. 53/28840

[51] Int. Cl.$^2$ .............................................. C07G 7/04
[52] U.S. Cl. ................................ 424/177; 260/112 R; 424/195
[58] Field of Search ................... 260/112 R; 424/177, 424/195

[56] References Cited

U.S. PATENT DOCUMENTS

| 3,637,396 | 1/1971 | Hollo et al. ..................... 260/112 X |
| 3,684,520 | 8/1972 | Bickoff et al. ................... 260/112 X |
| 3,823,128 | 7/1974 | Bickoff et al. ....................... 260/112 |
| 3,959,246 | 5/1976 | Bickoff ................................ 260/112 |
| 3,975,546 | 8/1976 | Stahmann ..................... 260/112 X |
| 4,066,633 | 1/1978 | Gastrneau et al. ................. 260/112 |

OTHER PUBLICATIONS

Chem. Abstracts, vol. 61, 1964, 6277c, Melteva et al.

*Primary Examiner*—Howard E. Schain
*Attorney, Agent, or Firm*—Haight & Huard

[57] ABSTRACT

Anti-mutagenic factor is fractionated from cabbage juice. The factor is a protein having an M. W. of about 48,000 when determined by the SDS-gel electrophoresis and shows characteristic adsorptions at 280 nm and 404 nm. The factor substantially inhibits the mutagenic activity of various mutagens such as pyrolysates of amino acids.

6 Claims, 2 Drawing Figures

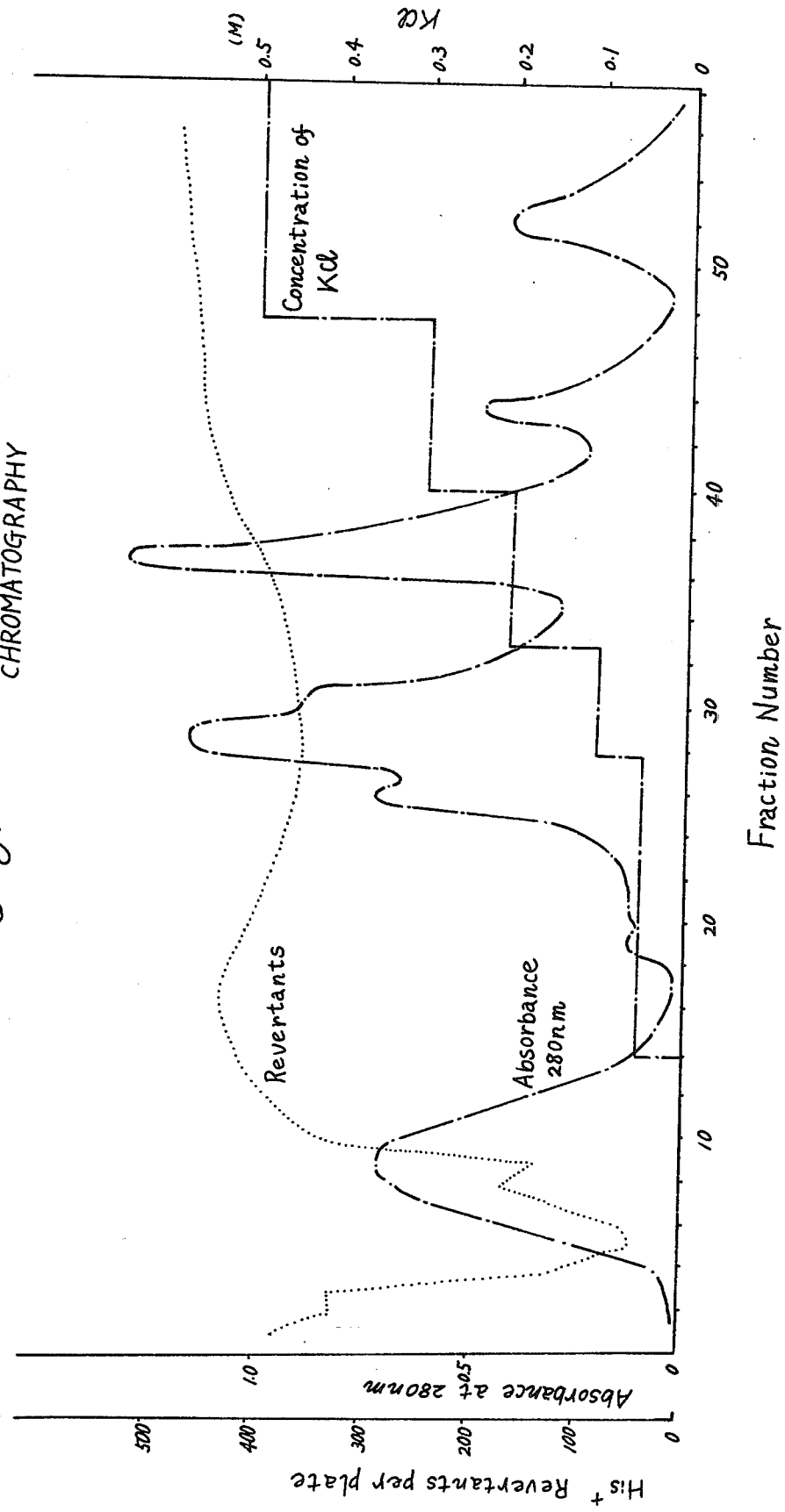
Fig. 1  DEAE-CELLULOSE COLUMN CHROMATOGRAPHY

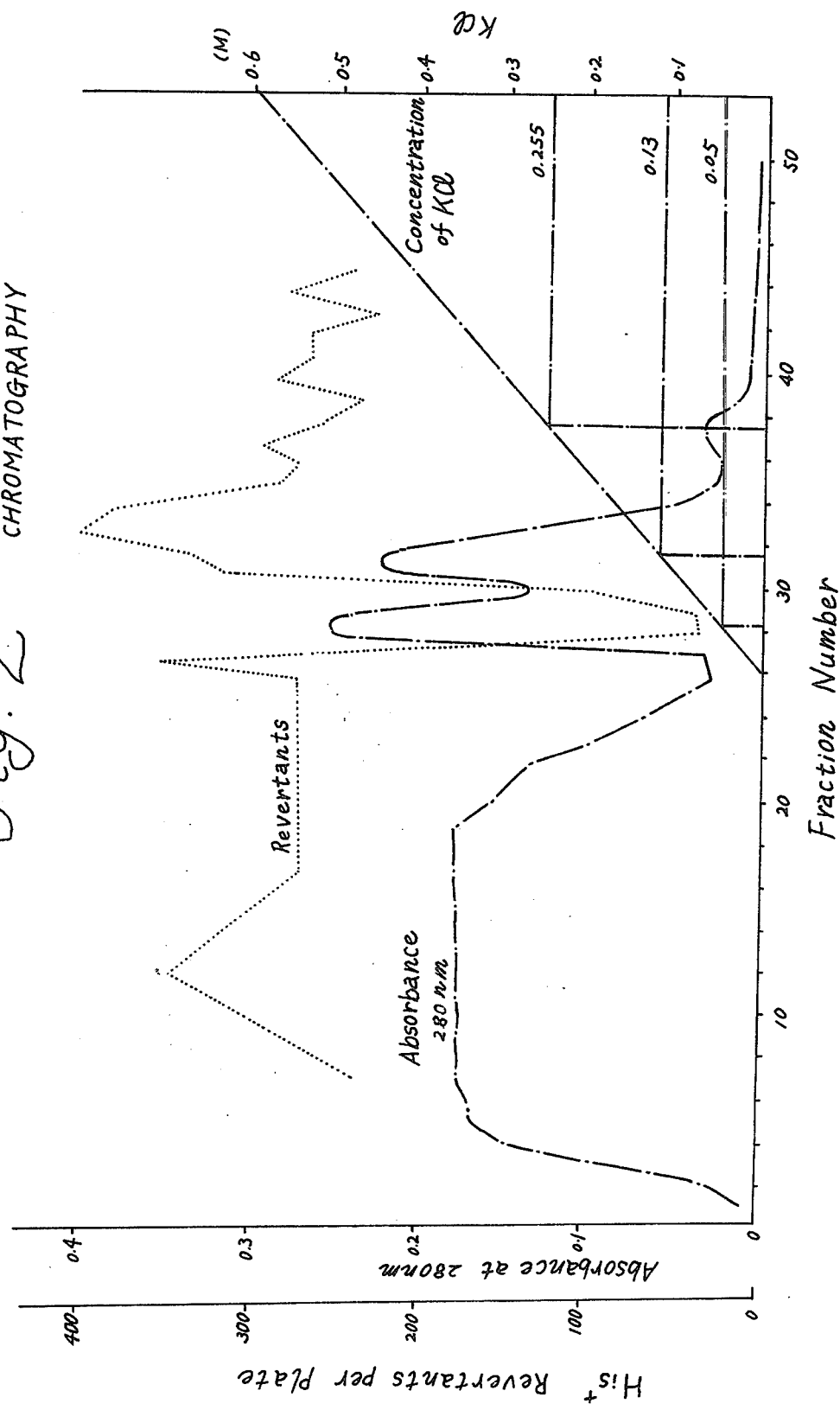
Fig. 2  CM-CELLULOSE COLUMN CHROMATOGRAPHY

ISOLATION OF ANTI-MUTAGENIC FACTOR FROM CABBAGE JUICE

This invention relates to a method for isolating an anti-mutagenic factor from cabbage juice.

It has been known that N-butyl-N-acetoxymethylnitrosoamine, reaction products of sorbic acid with nitrous acid, 2-aminoanthracene, ethidium bromide, and pyrolysates of amino acids such as tryptophan or ornithine are mutagens or carcinogens.

We have found that cabbage juices contains a factor which substantially inhibits the mutagenic activity of said mutagenic substances such as tryptophan pyrolysates and that said factor may be isolated in the substantially pure state by the fractionation of cabbage juice.

It is, therefore, an object of the present invention to provide a method for isolating the anti-mutagenic factor from cabbage juice effectively in the substantially pure state.

According to the present invention, said anti-mutagenic factor is isolated by the steps of;
(a) centrifuging cabbage juice to remove particles of tissue,
(b) ultracentrifuging the resulting supernatant,
(c) contacting the resulting supernatant with an anion exchange cellulose,
(d) applying the passed fraction to a column of a cation exchange cellulose,
(e) eluting the adsorbed substances with an aqueous eluant containing KCl or NaCl,
(f) separating from the eluate the fraction containing said anti-mutagenic factor which is eluted at a lower concentration of KCl or NaCl,
(g) applying said factor onto a molecular sieve, and
(h) recovering said factor therefrom.

In a preferred embodiment of the present invention, the supernatant resulting from step (b) may be subjected, prior to step (c), to dialysis or gel filtration to remove lower molecules therefrom. The dialysis may be carried out, for example, against 50 mM HEPES(-chemically, N-2-hydroxyethylpiperazine-N'-2-ethanesulfonic acid) or 50 mM phosphate buffer using a cellophane membrane. Molecular sieves for use in the gel filtration are selected from those capable of adsorbing molecules having an M.W. of less than about 1,000.

It is also preferable that the fraction resulting from step (f) is subjected to ultrafiltration and that all steps are carried out at a temperature below 5° C.

Examples of the anion exchange cellulose which may be employed in step (c) of the present invention include DEAE-cellulose, TEAE-cellulose and AE-cellulose. Examples of the cation exchange cellulose for use in step (d) include CMC, P-cellulose and PPM cellulose. Examples of the molecular sieves which may be employed in step (g) of the present invention include Sephacryl S-200, Sephadex G-75 and Biogel P-30. Examples of the filter membranes for use ultrafiltration include UM-10, UM-20E, PM-30 and other membranes through which molecules having an M.W. of less than 30,000 can pass.

The anti-mutagenic factor which may be isolated by the method of the present invention shows characteristic absorptions at 280 nm and 404 nm. The factor is stable to heating but deactivated by the action of a proteolytic enzyme. It is a protein having a molecular weight of about 48,000 when determined by the sodium dodecyl sulfate-gel (SDS-gel) electrophoresis.

The amino acid composition thereof in terms of molar percent is as follows:

| | |
|---|---|
| Asp | 13.22 |
| Thr | 8.43 |
| Ser | 6.70 |
| Glu | 6.38 |
| Pro | 6.56 |
| Gly | 7.22 |
| Ala | 9.89 |
| Cys | 1.73 |
| Val | 5.77 |
| Met | 1.29 |
| Ileu | 3.44 |
| Leu | 11.64 |
| Tyr | 1.31 |
| Phe | 5.36 |
| Lys | 2.59 |
| His | 1.07 |
| Arg | 7.40 |

The following example will further illustrate the present invention.

EXAMPLE 2000 g of cabbage leaves was washed with water and treated with a juicer at 0° C. to obtain cabbage juice. The juice was centrifuged at 9000 G at 4° C. for 30 minutes to remove tissue particles such as chloroplast or mitochondria. The supernatant was further ultracentrifuged at $2 \times 10^5$ G at 4° C. for 2 hours to remove finer particles such as microsome or ribosome. The resulting supernatant (528 ml) was dialysed against 50 mM HEPES buffer (pH 6.8) through a cellophane membrane to remove molecules having an M.W. of less than about 1,000. The dialysis solution was replaced twice.

The resulting dialysate was applied to a column of DEAE-cellulose (4 cm × 37 cm) at a flow rate of 122 ml/hour. The column was eluted at 4° C. with 50 mM HEPES buffer (pH 6.8) containing KCl in an amount increasing stepwise from 0 to 500 mM. Each fraction (15 ml/tube) of the eluate was tested for $A_{280}$ absorbance and the anti-mutagenic activities in accordance with the method which will be described in detail hereinafter. The anti-mutagenic activity was found only in the fraction which had not adsorbed onto DEAE-cellulose, i.e. at a KCl concentration of 0. The elution curve is shown in FIG. 1 of the accompanying drawings.

The foregoing fraction (1100 ml) was then applied to a column of CMC (2.5 cm × 8 cm) at a flow rate of 69 ml/hour. The column was eluted at 4° C. with 50 mM HEPES buffer (pH 6.8) containing KCl in an amount increasing continuously in a gradient from 0 to 500 mM. The eluate was collected in aliquots of 3 ml per tube. Each fraction were tested for $A_{280}$ absorbance and the anti-mutagenic activities as hereinbefore stated. The anti-mutagenic activity was found in fractions having a peak of the absorbance at a KCl concentration of 0.05 M. The elution curve is shown in FIG. 2 of the accompanying drawings. Thus, seven aliquots (21 ml) of the fractions having the anti-mutagenic activity were separated.

These fractions were incorporated together and subjected to ultrafiltration through a UM-10 filter to concentrate the fractions into 2.0 ml. The concentrate was then applied to a column of Sephacryl S-200 (1 cm × 92 cm). The column was then eluted with 50 mM tris-HCl buffer (pH 8.0) at 4° C. The eluate was collected in aliquots of 40 drops per tube. Each fraction was tested for 280 nm absorbance and the anti-mutagenic activity as hereinbefore stated. The anti-mutagenic activity was found in the second fraction of the eluate.

In order to know the purification degrees of the factor at each stage of foregoing process, the ratios of the anti-mutagenic activity to protein content were compared. From the comparison it was found that the activity was increased by about 200 times and about 450 times higher than that of the starting cabbage juice by the CMC column chromatography and the Sephacryl treatment, respectively.

The anti-mutagenic factor thus isolated was relatively stable to heating. For example only 50% of the activity thereof was lost upon heating at 100° C. for 90 minutes. The activity was lost entirely by the action of a proteolytic enzyme. The molecular weight was determined as about 48,000 by the SDS-gel electrophoresis. The factor has a characteristic absorbance at 404 nm as a Soret band which is peculiar to hemoproteins. Said Soret band will shift to 436.5 nm when the factor is treated with sodium hydrosulfite. This phenomenon indicates the transformation of the hemoprotein from the oxidized form ($Fe^{3+}$) to the reduced form ($Fe^{2+}$). From the foregoing, it is concluded that the factor is a hemoprotein.

Anti-mutagenic activity

10 μg of pyrolysate of tryptophan in 0.02 ml of DMSO is added to 0.5 ml of the fraction to be tested. The mixture is incubated at 37° C. for 30 minutes then heated at 100° C. for 10 minutes to deactivate the residual anti-mutagenic factor. To the mixture are added 3 ml of soft agar (0.5% Difco Agar) and 0.1 ml of a suspension of Salmonella TA98 (histidineless, His−). This mixture and 0.3 ml of S-9 Mix containing liver microsome of PCB-treated SD rat liver and having the hereinafter-described composition are poured onto an agar medium having the hereinafter-described composition and then incubated at 37° C. for 2 days. Colonies of revertants (histidine non-requiring, His+) are counted. The anti-mutagenic activity may be determined by comparing the number of colonies of the revertants with that of the control which is between 300 to 400 per plate.

| Composition of S-9 Mix: | |
|---|---|
| Liver microsome | 3.0 ml |
| 0.25 M $Na_2HPO_4$ | 4.0 ml |
| 0.16 M $MgCl_2$ | 0.5 ml |
| 0.66 M KCl | 0.5 ml |
| 0.05 M G-6-P | 1.0 ml |
| 0.04 M NADP | 1.0 ml |
| Composition of Agar Medium: | |
| MM(× 20) | 50 ml |
| 40% glucose | 10 ml |
| Difco Nutrient Broth 0.8% | 10 ml |
| Biotin (100γ/ml) | 1 ml |
| Agar | 15 g |
| Distilled water | 930 ml |
| Composition of MM(× 20): | |
| $(NH_4)_2SO_4$ | 2.0% |
| $KH_2PO_4$ | 20.0% |
| $MgSO_4 \cdot 7H_2O$ | 0.2% |
| Sodium citrate | 1.0% |
| pH 7.0 with KOH | |

We claim:

1. A method for isolating an anti-mutagenic factor from cabbage juice, which comprises the steps of:
   (a) centrifuging cabbage juice to remove particles of tissue including chloroplasts and mitochondria,
   (b) ultracentrifuging the resultant supernatant to remove microsomes and ribosomes,
   (c) contacting the resulting supernatant with an anion exchange cellulose to collect a fraction which has not been adsorbed onto said anion exchange cellulose,
   (d) applying the resultant fraction to a column of a cation exchange cellulose,
   (e) eluting the adsorbed substance with an aqueous eluant containing KCl or NaCl in a gradient concentration,
   (f) retaining a fraction which has an absorbance peak at 280 nm containing said anti-mutagenic factor which is eluted at a KCl or NaCl concentration of 0.05 M,
   (g) applying the resultant fraction onto a column of a molecular sieve, and
   (h) eluting said column with a buffer at pH 8.0 and collecting a fraction containing an anti-mutagenic factor which strongly inhibits the reverse mutation of histadineless Salmonella TA98 to histadine non-requiring Salmonella TA98 induced by a mutagen.

2. The method according to claim 1, wherein the supernatant resulting from step (b) is subjected to dialysis or gel-filtration prior to step (c).

3. The method according to claim 1 or claim 2, wherein the fraction resulting from step (f) is subjected to ultrafiltration prior to step (g).

4. The method according any one of the preceding claims, wherein all procedures are carried out at a temperature below 5° C.

5. Substantially pure anti-mutagenic factor consisting essentially of a hemoprotein isolated from cabbage juice and having, in its substantially pure form, a molecular weight of about 48,000 when determined by the sodium dedecylsulfate-gel electrophoresis, and the following amino acid composition in terms of molar percent:

| Asp | 13.22 |
|---|---|
| Thr | 8.43 |
| Ser | 6.70 |
| Glu | 6.38 |
| Pro | 6.56 |
| Gly | 7.22 |
| Ala | 9.89 |
| Cys | 1.73 |
| Val | 5.77 |
| Met | 1.29 |
| Ileu | 3.44 |
| Leu | 11.64 |
| Tyr | 1.31 |
| Phe | 5.36 |
| Lys | 2.59 |
| His | 1.07 |
| Arg | 7.40 | said factor having characteristic absorptions at 280 nm and 404 nm as a Soret band which shifts to 436.5 nm when said factor is treated with sodium hydrosulfite.

6. A method for removing the mutagenic activity of a mutagenic substance susceptible thereto which comprises contacting said substance with a mutagenic inhibiting concentration and amount of the hemoprotein according to claim 5.

* * * * *